US005462546A

United States Patent [19]
Rydell

[11] Patent Number: 5,462,546
[45] Date of Patent: Oct. 31, 1995

[54] BIPOLAR ELECTROSURGICAL FORCEPS

[75] Inventor: Mark A. Rydell, Golden Valley, Minn.

[73] Assignee: Everest Medical Corporation, Minneapolis, Minn.

[21] Appl. No.: 13,852

[22] Filed: Feb. 5, 1993

[51] Int. Cl.⁶ ............................................. A61B 17/39
[52] U.S. Cl. ................................... 606/51; 606/48
[58] Field of Search .................... 606/48, 50, 51, 606/52, 170, 174; 128/751

[56] References Cited

U.S. PATENT DOCUMENTS

| | | | |
|---|---|---|---|
| 3,651,811 | 3/1972 | Hildebrandt et al. | 606/51 |
| 3,920,021 | 11/1975 | Hillebrandt . | |
| 4,003,380 | 1/1977 | Wien . | |
| 4,005,714 | 2/1977 | Hillebrandt . | |
| 4,041,952 | 8/1977 | Morrison, Jr. et al. . | |
| 4,461,305 | 7/1984 | Cibley . | |
| 4,657,016 | 4/1987 | Garito et al. . | |
| 4,763,669 | 8/1988 | Jaeger | 128/751 |
| 4,938,761 | 7/1990 | Enselin . | |
| 5,009,661 | 4/1991 | Michelson . | |
| 5,026,370 | 6/1991 | Lottick . | |
| 5,078,717 | 1/1992 | Parins et al. . | |
| 5,082,000 | 1/1992 | Picha et al. | 128/751 |
| 5,133,727 | 7/1992 | Bales et al. | 606/170 |
| 5,147,357 | 9/1992 | Rose et al. | 606/51 |
| 5,324,289 | 6/1994 | Eggers | 606/48 |
| 5,330,471 | 7/1994 | Eggers | 606/48 |

FOREIGN PATENT DOCUMENTS

| | | | |
|---|---|---|---|
| 517244 | 12/1992 | European Pat. Off. | 606/50 |
| 518230 | 12/1992 | European Pat. Off. | 606/48 |
| 598149 | 12/1925 | France | 606/50 |
| 2808911 | 3/1979 | Germany . | |
| 3709067 | 9/1988 | Germany . | |
| 575103 | 6/1977 | U.S.S.R. | 606/48 |
| 649420 | 3/1979 | U.S.S.R. . | |

OTHER PUBLICATIONS

U. S. Statutory Invention Reg. No. H1028 Falk et al., Mar. 2, 1992.
"Two New Laparoscopic Instruments: Bipolar Sterilizing Forceps and Uterine Manipulator", by Stephen L. Corson, Medical Instrumentation, vol. 11, No. 1.
Cameron—Miller Product Brochure for Model 80–7527.

*Primary Examiner*—Lee S. Cohen
*Attorney, Agent, or Firm*—Haugen and Nikolai

[57] ABSTRACT

A hand operable bipolar forceps instrument comprising two interfacing pivotal blade member's which are each an electrode individually pivotable in relation to each other. Pivotal movement of the blades is effectuated by two respective electrically-conductive rigid rods, each coupled to a respective blade member, extending through an elongated tubular member having disposed at its proximal end a scissors type handle whose hand operation causes the blade members to pivot in relation to each other. The rods are connectable proximally to an energy source to thereby electrically activate the blade members.

3 Claims, 2 Drawing Sheets

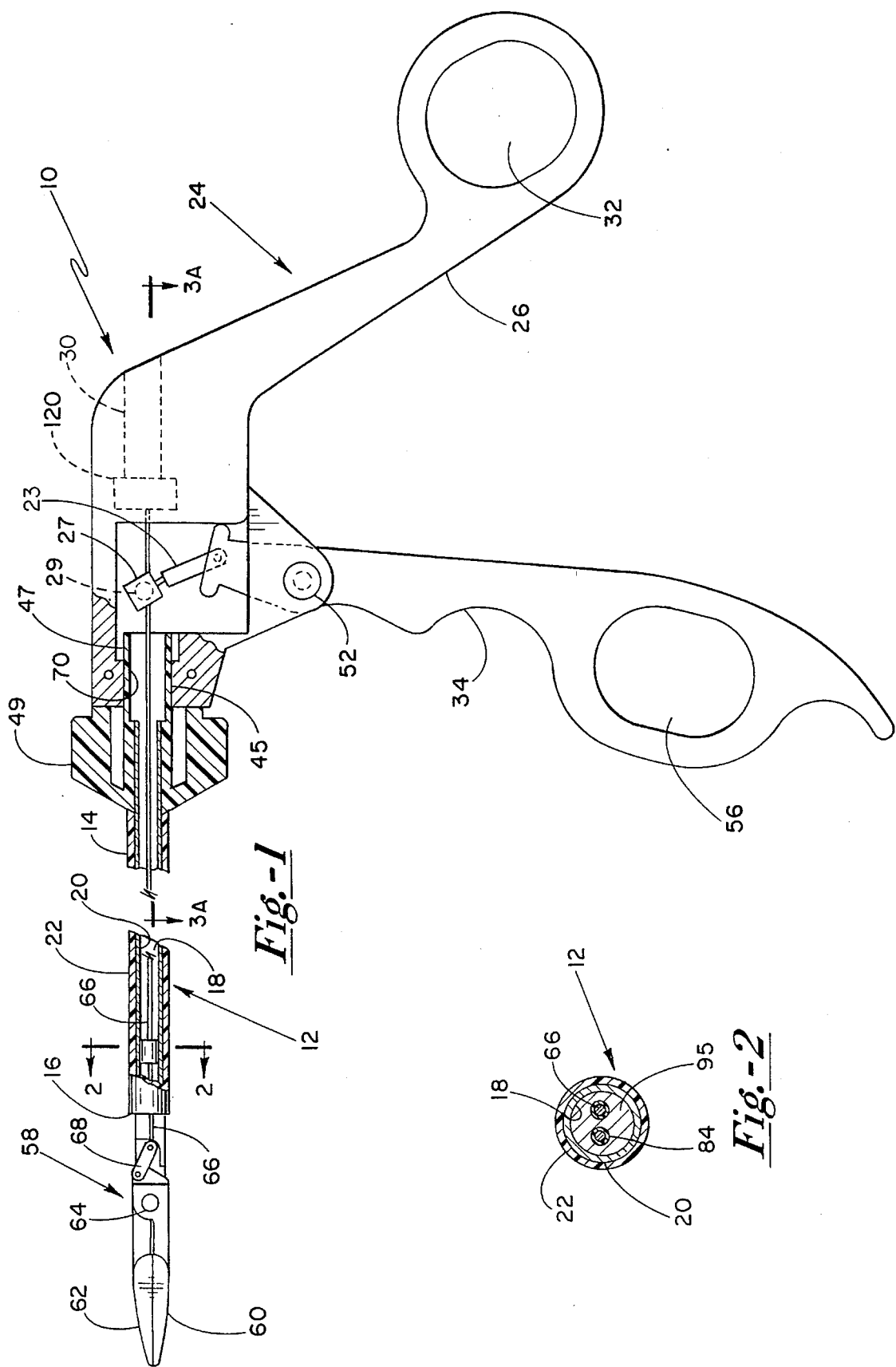

BIPOLAR ELECTROSURGICAL FORCEPS

BACKGROUND OF THE INVENTION

I. Field of the Invention

This invention relates generally to surgical forceps, and in particular to bipolar forceps wherein both blade members thereof pivot individually and are electrodes to thereby selectively provide direct electrocoagulation of tissue being grasped without requiring the introduction of a separate coagulation instrument to the surgical site.

II. Discussion of the Prior Art

Electrocauterization is a process whereby blood vessels (commonly called "bleeders") cut during a surgical procedure are sealed closed by applying electrical energy at the site to, essentially, fuse by heat the vessel opening. In order to provide electrical energy at the site of bleeding, an instrument capable of conducting electricity must be placed at that site. The conductive instrument may be comprised of one electrode (monopolar) which cooperates with a remote conductive body plate electrode, or the instrument may be comprised of two closely spaced electrodes (bipolar). Current passing from one electrode to the other produces the heat sufficient to seal blood vessels or to coagulate blood and other fluids so coagulable. A bipolar instrument is generally preferred by a physician since current travel is over a short distance. A monopolar instrument usually requires electric current to travel a relatively long distance to the body plate electrode, with current directability and effect being unpredictable and possibly harmful to a patient.

Surgical scissors are known in the art. Those available for use in endoscopically performed surgeries, for example, are of a size to fit distally through the endoscope while having operating handles proximally of the endoscope. Generally, the scissors include a proximal scissors-type handle, a central hollow tube through which a linkage from the handle passes, and a distal blade pair to which the linkage connects. Monopolar scissors, wherein both of the scissor blades form one pole and a remote body plate as the second pole, are available. Co-pending and commonly assigned patent application Ser. No. 887,212, filed May 21, 1992, now abandoned, and incorporated herein by reference, teaches a bipolar scissors instrument where each blade thereof is a pole and wherein only one of the scissors' blades pivots in relation to the other blade. A ceramic layer is present on each of the respective inner surfaces of each blade member, and insulation means at strategic sites throughout the instrument maintain bipolar capability for the separate blade members. Bipolar forceps having attributes which permit employment in endoscopic, laparoscopic and other lumen/scope procedures would provide similar benefits for the user.

In view of the above discussed prior art, it is a primary object of the present invention to provide bipolar forceps having two blade members wherein each blade member pivots in relation to the other.

It is a further object of the present invention to provide a forceps instrument which exhibits bipolarity for selective application of electrocauterization at a surgical site.

These and other objects of the present invention will become apparent in the description of the invention which follows.

SUMMARY OF THE INVENTION

The present invention is a hand operable forceps instrument comprising two interfacing pivotable blade members which are each an electrode to which current can flow, and further wherein each blade member is individually pivotable in relation to the other blade member. In the forceps instrument constructed according to the present invention, the blade members meet to produce a pinching or gripping action. Pivotal movement of the blades is effectuated by two respective rigid rods, each coupled to a respective blade member, extending through a proximally disposed elongated tubular member having disposed at its proximal end a scissors type handle whose hand operation causes the blade members to pivot in relation to each other. Current is delivered to the blades through the rods which are connectible to an RF source and which are electrically insulated throughout the instrument. In this manner, a bipolar instrument having cauterization properties, clamping properties and tissue dissection properties is provided for deployment to the site of a surgical procedure.

BRIEF DESCRIPTION OF THE DRAWINGS

FIG. 1 is a side elevation view of a forceps instrument having two movable blades, the drawing being partially sectioned to illustrate the working elements of the embodiment;

FIG. 2 is a cross-section view along line 2—2 of FIG. 1;

DETAILED DESCRIPTION OF A PREFERRED EMBODIMENT

Figure 3A:
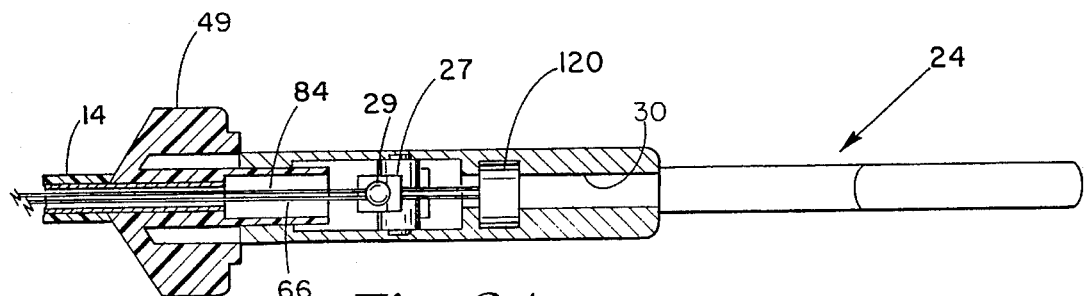
FIG. 3a is a partial top plan view of the proximal portion of FIG. 1.

Referring to FIG. 1, a bipolar electrosurgical forceps 10 is shown for use in endoscopic or other similar scope-type procedures. The forceps 10 has an elongated tubular member 12 of a diameter and length sufficient for use in cooperation with a procedure performed employing scope-type instrumentation. The tubular member 12 has a proximal end 14, a distal end 16 and a lumen 18 which extends for the entire length of the tubular member 12. As shown in the cross-sectional view of FIG. 2, the tubular member 12 comprises a metal tube 20 coated with an electrical insulator 22. The electrical insulator 22 is preferably a polymer such as Teflon®. In addition to being an insulator, such a coating provides a lubricous surface which enhances its slidability through the lumen of an endoscope.

Figure 3B:
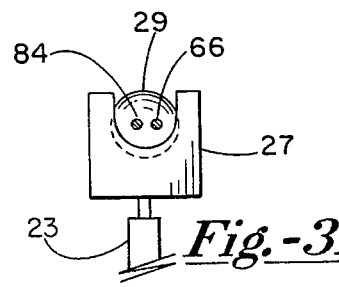
FIG. 3b is a front elevation view of a portion of a coupling for moving the two movable blades.

Disposed at the proximal end 14 of the tubular member 12 is a scissors-type handle assembly 24. The handle assembly 24 has a first handle member 26 having first and second ends, with the first end thereof having a bore 30 extending therethrough and wherein, at the distal portion thereof, the proximal end 14 of the tubular member 12 resides. The first handle member 26 does not pivot. At its second end the first handle member 26 has a loop 32 intended to receive the thumb of an operator. The handle assembly 24 additionally has a second handle member 34 which is pivotable with respect to the first handle member 26 by being pivotally mounted to the first handle member 26 with a pivot pin 52. The first end of the second handle member 34 has pivotally mounted thereto by pivot pin 23 an open top, U-shaped cradle member 27 shown in detail in FIGS. 3a and 3b in which is cradled a sphere 29 in indirect communication with the distal blade members as described later. Situated at the second end of the handle member 34 is a loop 56 to receive the forefinger of the operator.

Press fit into the distal end 16 of the tubular member 12 is a forceps blade assembly 58. As will be explained more fully later, the blade assembly 58 comprises a first blade member 60 and a second blade member 62 pivotally joined to each other by an insulated rivet or screw 64 which extends through bores formed through the two blade members 60, 62. Both blade members 60, 62 are pivotally movable with respect to each other.

Figure 4:
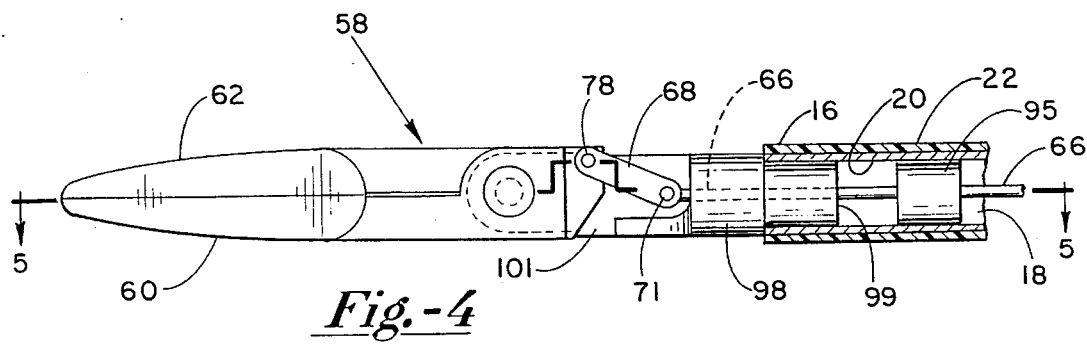
FIG. 4 is an enlarged side elevation view of the distal portion of FIG. 1.
Figure 5:
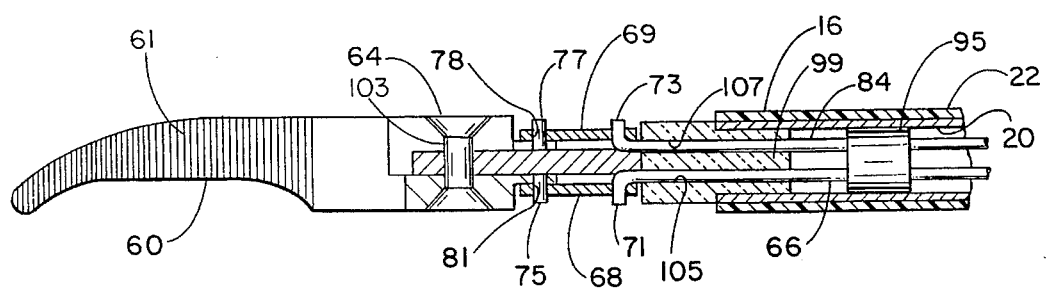
FIG. 5 is a cross-section view along line 5—5 of FIG. 4.

With reference to FIGS. 1 and 2, it is seen that two rigid electrically conductive rods 66, 84, each preferably covered with a layer of electrical insulation, extend through the lumen 18 of the tubular member 12. Referring to FIGS. 1, 4 and 5, which show the distal portion of the forceps 10, the rods 66, 84 are pivotally coupled to the respective blade members 60, 62 by respective rigid links 68, 69. The distal ends of the rods 66, 84 are turned laterally outwardly to fit through respective proximal pivot point openings, 71, 73 of the links 68, 69 to thereafter form a rivet type connection. Situated at each of the proximal portions of the blade members 60, 62 in step-down sections thereof are laterally projecting posts 75, 77 which pass through distal pivot openings 78, 81 of the links 68, 69 to likewise form rivet type connections. The rigid links 68, 69 thereby can pivot at each of their respective proximal and distal end portions.

As is evident in FIGS. 4 and 5, the forceps blade assembly 58 comprises, in addition to the blade members 60, 62, an insulated base 98 having a proximal portion 99 and a distal portion 101. The distal portion 101 has a bore 103 therethrough which provides a frame to which the blade members 60, 62 are pivotally attached via the pin or screw 64. The proximal portion 99 of the base 98 is press fit within the tubular member 12 and has two parallel longitudinal bores 105, 107 through which the rods 66, 84 pass. Proximal to the base 98 within the tubular member 12 is disposed and insulator member 95 through which the rod 66, 84 pass. This insulator member 95 functions to electrically isolate the rod 66, 84 from each other while mechanically acting to maintain them together.

The respective proximal ends of the rods 66, 84 extend proximally from the proximal end of the tubular member 12 through the sphere 29 (FIGS. 3*a* and 3*b*) and terminate in a free-wheeling electrical connector 120. The free-wheeling connector 120 cannot move translationally in the handle assembly 24, but can freely rotate. External leads originating from an electrosurgical generator (not shown) as known in the art provide current to connector 120 to thereby provide current to the rods 66, 84.

Because the sphere 29 is freely rotatable within the cradle member 27, the tubular member 12, and therefore the blade members 60, 62, can be rotatably moved. A knob 49 is therefore provided near the proximal end of the tubular member 12 to facilitate easy rotation by hand of the blade members 60, 62 when blade member positioning is performed by the operator. As seen in FIG. 1, the rotatable knob 49 is generally cylindrical in shape, having a bore 70 through its center along the central axis. The bore 70 is large enough to accept the tube 20 therein and allow the conductive rods 66, 84 to pass therethrough. The proximal end of the tube 20 is frictionally inserted into the bore 70, to thereby rotate when the knob 49 is rotated. The knob 49 has an integrally formed tubular extension 45 which terminates in an annular flange 47. The handle assembly 24 has complementarily shaped internal contours which accept the extension 45 and the flange 47 to thereby allow rotation thereof within the handle assembly 24. The knob 49 is preferably constructed of nylon so that the extension 45 and annular flange 47 will have lubricous characteristics for smoother rotation inside of the handle assembly 24. Because the rods 66, 84 are mechanically connected by the insulator member 95 which is stationary within the tube 20, rotation of the knob 49 results in rotation of the tube 20 as well as the rods 66, 84 to thereby also rotate the blade members 60, 62. Concurrently, the sphere 29 is rotated because the rods 66, 84 pass therethrough to their termination in the free-wheeling electrical connector 120. As is evident from FIG. 1, operation of the handle assembly 24 by pivotally moving the second handle member 34 moves the cradle member 27 to thereby translationally move the sphere 29 which in turn moves both of the rods 66, 84 to thereby pivotally open and close the blade member 60, 62. In this manner, dual blade movement is accomplished.

Referring to FIGS. 4 and 5, each blade member 60, 62 of the forceps 10 is preferably stainless steel. The blade member 60, 62 can be conformed of any shape as desired to provide a grasping action typical of a forceps' behavior. A vessel or tissue held within the blade members 60, 62 becomes cauterized when the operator applies current to thereby activate the bipolar activity of the blade members. Upon completion of the procedure, current delivery is terminated and the interfacing surfaces of the blade members 60, 62 are opened upon operation of the handle assembly 24 to thereby release the treated site. The mating surfaces of the blades 60, 62 can have serrations 61 to improve gripping ability.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

I claim:

1. A hand operable bipolar forceps instrument comprising:
    (a) an elongated tubular member having a proximal end, a distal end, and a lumen extending therebetween;
    (b) two interfacing pivotable blade members disposed at the distal end of the tubular member, said blade members each being an electrode to which current can flow, and further wherein each blade member is individually pivotable in relation to the other blade member from an open position to a closed position;
    (c) a handle disposed at the proximal end of the tubular member, said handle being in communication with the blade members and being hand operable to thereby produce pivotal action of the blade members; and
    (d) means for journaling the proximal end of the elongated tubular member for rotation in the handle, rotation of the tubular member effecting rotation of the blade members relative to the handle.

2. The instrument as claimed in claim 1 wherein each blade member is a metal.

3. The instrument as claimed in claim 2 wherein the metal is stainless steel.

\* \* \* \* \*